(12) United States Patent
Nagare et al.

(10) Patent No.: US 10,729,631 B2
(45) Date of Patent: Aug. 4, 2020

(54) OIL-IN-WATER EMULSION COMPOSITION

(71) Applicant: SHISEIDO COMPANY, LTD., Chuo-ku, Tokyo (JP)

(72) Inventors: Yuko Nagare, Yokohama (JP); Kazuhiro Yamaguchi, Yokohama (JP); Mayuri Tashiro, Yokohama (JP)

(73) Assignee: SHISEIDO COMPANY, LTD., Tokyo (JP)

( * ) Notice: Subject to any disclaimer, the term of this patent is extended or adjusted under 35 U.S.C. 154(b) by 15 days.

(21) Appl. No.: 15/321,597

(22) PCT Filed: Jun. 30, 2015

(86) PCT No.: PCT/JP2015/068774
§ 371 (c)(1),
(2) Date: Dec. 22, 2016

(87) PCT Pub. No.: WO2016/002751
PCT Pub. Date: Jan. 7, 2016

(65) Prior Publication Data
US 2017/0202758 A1    Jul. 20, 2017

(30) Foreign Application Priority Data
Jun. 30, 2014 (JP) ................................. 2014-133546

(51) Int. Cl.
*A61Q 19/00* (2006.01)
*A61K 8/58* (2006.01)
*A61K 8/06* (2006.01)
*A61K 8/25* (2006.01)
*A61Q 17/04* (2006.01)
*A61K 8/27* (2006.01)
*A61K 8/894* (2006.01)
*A61K 8/37* (2006.01)
*A61K 8/73* (2006.01)
*A61K 8/19* (2006.01)
*A61K 8/02* (2006.01)
*A61K 8/29* (2006.01)
*A61K 8/31* (2006.01)
*A61K 8/88* (2006.01)
*A61K 8/891* (2006.01)

(52) U.S. Cl.
CPC ............ *A61K 8/585* (2013.01); *A61K 8/0241* (2013.01); *A61K 8/062* (2013.01); *A61K 8/19* (2013.01); *A61K 8/25* (2013.01); *A61K 8/27* (2013.01); *A61K 8/29* (2013.01); *A61K 8/31* (2013.01); *A61K 8/37* (2013.01); *A61K 8/375* (2013.01); *A61K 8/73* (2013.01); *A61K 8/732* (2013.01); *A61K 8/88* (2013.01); *A61K 8/891* (2013.01); *A61K 8/894* (2013.01); *A61Q 17/04* (2013.01); *A61Q 19/00* (2013.01); *A61K 2800/48* (2013.01); *A61K 2800/621* (2013.01); *A61K 2800/622* (2013.01); *A61K 2800/624* (2013.01); *A61K 2800/651* (2013.01)

(58) Field of Classification Search
CPC ............ A61K 8/29; A61K 8/25; A61Q 17/04
See application file for complete search history.

(56) References Cited

U.S. PATENT DOCUMENTS

2003/0185771 A1    10/2003   Kamel et al.
2004/0147632 A1*   7/2004    Nakamura ............ C09D 11/16
                                                        523/160
2010/0172850 A1    7/2010    Mitsui

FOREIGN PATENT DOCUMENTS

| EP | 2002822 A2 * | 12/2008 | ............ A61K 8/064 |
|---|---|---|---|
| JP | 2002-255746 | 9/2002 | |
| JP | 2003-81770 | 3/2003 | |
| JP | 2006008796 A * | 1/2006 | |
| JP | 2007-119741 | 5/2007 | |
| JP | 2010-254673 | 11/2010 | |
| JP | 2011-236202 | 11/2011 | |
| JP | 2012-111726 | 6/2012 | |
| JP | 2012-162515 | 8/2012 | |
| JP | 2014-133553 | 6/2014 | |
| WO | WO 2004/006871 | 1/2004 | |
| WO | 2008-143823 | 6/2008 | |
| WO | PCT/JP2015/068776 | 6/2015 | |

OTHER PUBLICATIONS

Dekant, W. et al., "Toxicology of decamethylcyclopentasiloxane (D5)", Regulatory Toxicology and Pharmacology 74, 2016, S67-S76.*
Hasegawa, K. et al. "Oil-in-water type emulsion composition", JP 2006008796 A, Jan. 12, 2012, English machine translation.*
PCT/JP2015/068774, International Search Report and Written Opinion, dated Oct. 6, 2015, 2 pages—English, 7 pages—Japanese.
EP 15815470.8 Office Action dated Dec. 12, 2017, 7 pages—English.

* cited by examiner

Primary Examiner — Gina C Justice
(74) Attorney, Agent, or Firm — Andrew F. Young, Esq.; Lackenbach Siegel, LLP

(57) ABSTRACT

The purpose of the present invention is to provide an oil-in-water emulsion composition exhibiting high UV-protective capabilities with which it is possible to uniformly and stably disperse a hydrophobized metal oxide into an inner phase (oil phase) without detracting from the inherent fresh sensation on use of an oil-in-water emulsion composition even when a high amount of the hydrophobized metal oxide is compounded therewith. In summary, the present invention is an oil-in-water emulsion composition characterized by including (A) 0.1-5 mass % of polyether-modified silicone having an HLB (Si) of 5-14, (B) one or more hydrophilic thickeners, (C) a metal oxide hydrophobized by an agent other than metal soap, and (D) nonvolatile oil other than silicone oil, the (C) hydrophobized metal oxide being present in the inner phase.

7 Claims, 1 Drawing Sheet

OIL-IN-WATER EMULSION COMPOSITION

CROSS REFERENCE TO RELATED APPLICATIONS

This application relates to and claims priority as a § 371 national phase, from PCT/JP2015/068774 filed Jun. 30, 2016, the entire contents of which are incorporated herein by reference, which in turn claims priority from JP 2014-133546 filed Jun. 30, 2014.

TECHNICAL FIELD

The present invention relates to an oil-in-water emulsion composition. More specifically, the invention relates to an oil-in-water emulsion composition, particularly a sunscreen cosmetic, that achieves an excellent UV protection effect by homogeneously and stably dispersing a hydrophobically treated metal oxide in an internal phase (oil phase), without losing the fresh sensation in use that is inherent in oil-in-water emulsion compositions. The oil-in-water emulsion composition of the present invention maintains high dispersibility of hydrophobically treated metal oxides even after application to the skin or the like, and has excellent transparency of the formed film.

BACKGROUND ART

Oil-in-water emulsion compositions are widely used as bases in skin-care preparations for external use, such as skin-care cosmetics or the like, that are applied directly to the skin, because they provide a crisp and fresh sensation when applied to the skin. In particular, skin care and body care have come to include everyday protection of the skin from UV rays, and the importance of using oil-in-water emulsion compositions as bases in such UV-care cosmetics is also increasing.

On the other hand, while metal oxide powders are known to have the function of UV-scattering agents that protect the skin from UV rays, aside therefrom, they also have the functions of improving the feeling in use during application, and concealing coloration and blotches, freckles and the like on the skin, so they have conventionally been widely added to various types of cosmetics. In recent years, metal oxides having hydrophobically treated surfaces have been used for the purposes of improving water resistance, cosmetics durability and cosmetic dispersibility.

When blending a hydrophobically treated metal oxide powder such as hydrophobic fine-particle titanium oxide or hydrophobic fine-particle zinc oxide into an oil-in-water emulsion composition, it is usually dispersed in a volatile oil using a low-HLB dispersing agent or special dispersing equipment such as a wet bead mill with strong pulverization energy to be emulsified. However, in order to mix a lot of powder in order to obtain sufficient UV ray protection capability, a large quantity of oil becomes necessary for dispersing the powder, as a result of which the feeling in use can become oily and the freshness that is inherent in oil-in-water emulsion compositions can be lost. Additionally, if the dispersion medium of the powder evaporates after application to the skin, the powder can re-aggregate in the formed film and cause the lost transparency.

In sunscreen cosmetics, it is common to make combined use of UV-absorbing agents and UV-scattering agents such as metal oxide powders in order to achieve UV protection effects against a wide wavelength range from the UVA range to the UVB range, but most UV-absorbing agents are non-volatile oils, so the total oil content, when also adding the oils used as the powder dispersion medium, becomes high, and the relative water content decreases, making it difficult to achieve a fresh feeling in use.

For example, Patent Document 1 describes an oil-in-water emulsified sunscreen cosmetic wherein, in order to stably disperse a hydrophobically treated zinc oxide without using a special dispersion apparatus, a specific compound (octyltriethoxysilane or dimethylpolysiloxane) is used for the hydrophobic treatment of the zinc oxide, and this is dispersed in a specific oil (liquid higher fatty acid) using a specific dispersing agent (a carboxyl group-containing silicone or sugar ester). However, a large amount of volatile oil is required in order to stably disperse hydrophobically treated zinc oxide, as a result of which the total oil content increases and a fresh feeling in use is difficult to achieve.

Additionally, Patent Document 2 describes that, in order to stably blend hydrophobically treated powder particles into an oil-in-water emulsion composition that uses an ionic water-soluble polymer compound as a thickener, hydrophobic powder particles are used as the powder particles, and furthermore, ion elution is prevented by mixing a specific polyether-modified silicone into the oil phase.

In this composition, the polyether-modified silicone acts as a gelling agent for gelling the oil phase which includes a silicone oil and hydrophobic powder particles, and prevents ion elution from the hydrophobic powder particles in the oil phase, thereby stabilizing the thickening due to the ionic polymers in the water phase. However, since the dispersion of powder in an oil phase is conventionally performed by mechanical force and a large amount of silicone oil must be added as a dispersion medium in order to sufficiently disperse the hydrophobic powder particles, as with Patent Document 1, the total oil content increases and it is difficult to achieve a fresh feeling, in use.

On the other hand, aside from the above-mentioned Patent Document 2, there have been other attempts to achieve stabilization of ail-in-water emulsion compositions using polyether-modified silicones (Patent Documents 3 to 5). Patent Document 3 describes that a non-sticky, fresh sensation in use, stability and a high SPF can be achieved by mixing a combination of polyether-modified silicone, a predetermined amount of an extender pigment, and a UV-absorbing agent having absorption capability in the UV-A region. Patent Document 4 describes that excellent water resistance can be obtained after application to the skin, by forming an oil-in-water emulsion using a polyether-modified silicone having an HLB (Si) of 5 to 10 as a surfactant, and further adding a predetermined amount of ethanol, a hydrophilic thickener and a polyol. Patent Document 5 describes that, by blending an aqueous dispersion of an oil-soluble UV-absorbing agent into the water phase in a stable system similar to that of Patent Document 4, the UV protection effect was increased over the case of blending a UV-absorbing agent into an oil phase.

However, none of Patent Documents 3 to 5 teaches a method of blending a high content of a hydrophobically treated metal oxide. On the contrary, Patent Document 3 describes that the emulsion stability becomes worse when adding hydrophobically treated talc as compared with the case where talc that has not been hydrophobically treated is added (Comparative Example 4), and Patent Document 5 describes that the feeling in use is inferior when fine-particle titanium oxide is added (Comparative Example 2).

RELATED ART DOCUMENTS

Patent Documents

Patent Document 1: JP 2012-111726 A
Patent Document 2: WO 2004/006871
Patent Document 3: JP 2012-162515 A
Patent Document 4: JP 2010-254673 A
Patent Document 5: JP 2011-236202 A

SUMMARY OF THE INVENTION

Problems to be Solved by the Invention

The present invention was made in consideration of the above-mentioned drawbacks of the conventional art, and has the purpose of offering an oil-in-water emulsion composition which allows the homogeneous and stable dispersion of hydrophobically treated metal oxides without losing the fresh sensation in use that is inherent in oil-in-water emulsion compositions, and which has excellent transparency of the applied film.

Means for Solving the Problems

As a result of repeating diligent research into solving the above-mentioned problems, the present inventors discovered that a hydrophobically treated metal oxide can be homogeneously and stably blended without blending large amounts of silicone oils or volatile oils, and a fresh feeling in use can be maintained, by blending a polyether-modified silicone having a specific HLB (Si), a hydrophilic thickener, and a non-volatile oil other than a silicone oil, thereby completing the present invention.

In other words, the present invention is basically directed to an oil-in-water emulsion composition characterized by comprising:
(A) 0.1 to 5% by mass of a polyether-modified silicone having an HLB (Si) of 5 to 14;
(B) one or more hydrophilic thickeners;
(C) a metal oxide hydrophobically treated without using a metal soap; and
(D) a non-volatile oil other than a silicone oil;
wherein the (C) hydrophobically treated metal oxide is present in the internal phase.

Effects of the Invention

The oil-in-water emulsion composition according to the present invention, by using a combination of (A) a polyether-modified silicone with an HLB (Si) of 5 to 14 as dispersing agent with (B) a hydrophilic thickener and (D) a non-volatile oil other than a silicone oil, allows (C) a hydrophobically treated metal oxide to be homogeneously and stably blended into the internal phase (oil phase) of the oil-in-water emulsion composition. For this reason, there is no need to add large amounts of volatile oils or silicone oils in order to disperse the (C) hydrophobically treated metal oxide, and a high UV protection effect can be achieved while maintaining a fresh feeling in use. Additionally, since the dispersibility of the powder can be kept high even after application to the skin, the formed film has excellent transparency.

MODES FOR CARRYING OUT THE INVENTION

Figure 1:
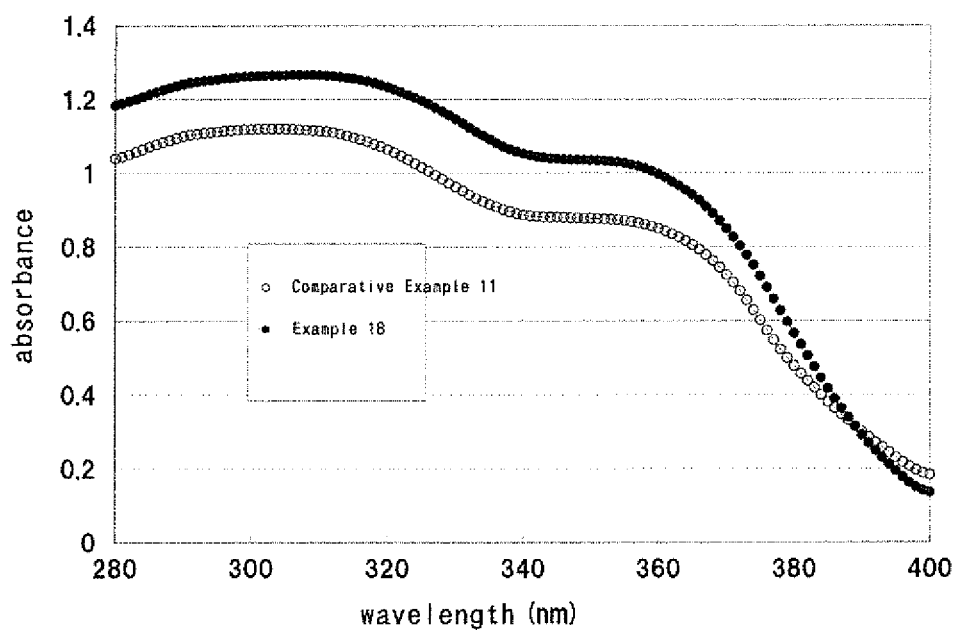
FIG. 1 A graph showing the UV shielding effect of Example 18 and Comparative Example 11.

The oil-in-water emulsion composition of the present invention comprises, as essential components, (A) a polyether-modified silicone having an HLB (Si) of 5 to 14; (B) a hydrophilic thickener; (C) a hydrophobically treated metal oxide; and (D) a non-volatile oil other than a silicone oil. Herebelow, the present invention will be described in detail.

<(A) Polyether-Modified Silicone Having an HLB (Si) of 5 to 14>

The (A) polyether-modified silicone in the oil-in-water emulsion composition of the present invention is a silicone derivative having a polyoxyalkylene group selected from the group consisting of polyoxyethylenes (POE) and polyoxypropylenes (POP). In particular, the polyether-modified silicones represented by the following general formula are preferred.

[Chemical Formula 1]

$$H_3C-\underset{\underset{CH_3}{|}}{\overset{\overset{CH_3}{|}}{Si}}-\left[\underset{\underset{CH_3}{|}}{\overset{\overset{CH_3}{|}}{OSi}}\right]_m-\left[\underset{\underset{(CH_2)_3O(C_2H_4O)_a(C_3H_6O)_bH}{|}}{\overset{\overset{CH_3}{|}}{OSi}}\right]_n-\underset{\underset{CH_3}{|}}{\overset{\overset{CH_3}{|}}{OSi}}-CH_3$$

In the above formula, m is 1 to 1000, preferably 5 to 500, and n is 1 to 40. Additionally, m:n is preferably 200:1 to 1:1. Additionally, a is 5 to 50 and b is 0 to 50.

The molecular weight of the polyether-modified silicone is not particularly limited, but should preferably be in the range of 3,000 to 60,000, and more preferably 3,000 to 40,000. A particularly excellent feeling in use can be achieved by using a low molecular weight polyether-modified silicone.

The polyether-modified silicone used in the present invention is selected from those having an HLB (Si) of 5 to 14, more preferably 7 to 14. The HLB (Si) mentioned here is a value determined by the following computational formula:

$$\frac{\text{Molecular weight of polyoxyethylene } (POE) \text{ and polyoxypropylene}(POP)}{\text{Molecular weight}} \times 20 \quad \text{[Equation 1]}$$

As the (A) polyether-modified silicone, one or more types selected from those that are conventionally used in cosmetics and the like may be used. Specific examples include PEG/PPG-19/19 dimethicone, PEG/PPG-30/10 dimethicone, PEG-12 dimethicone and PEG-11 methyl ether dimethicone.

The (A) polyether-modified silicone used in the present invention may be commercially available, for example:
Product name BY11-030 (manufactured by Toray Dow Corning: PEG/PPG-19/19 dimethicone, HLB (Si)=7.7)
Product name SH3773M (manufactured by Toray Dow Corning: PEG-12 dimethicone, HLB (Si)=7.7)
Product name BY25-339 (manufactured by Toray Dow Corning: PEG/PPG-30/10 dimethicone, HLB (Si)= 12.2)

Product name KF6011 (manufactured by Shin-etsu Chemical: PEG-11 methyl ether dimethicone, HLB (Si)=12.7)

The blended amount of the (A) polyether-modified silicone should preferably be at least 0.1% by mass, at least 0.2% by mass, at least 0.3% by mass, at least 0.4% by mass or at least 0.5% by mass, and at most 5% by mass, at most 4% by mass or at most 3% by mass with respect to the total amount of the oil-in-water emulsion composition of the present invention. The specific range of the blended amount should be 0.1 to 5% by mass, preferably 0.5 to 5% by mass, and more preferably 0.5 to 3% by mass. If the blended amount is less than 0.1% by mass, there may be cases in which a stable composition in which the (C) hydrophobically treated metal oxide is not homogeneously dispersed, and a stable oil-in-water emulsion composition cannot be obtained, and if more than 5% by mass is blended, the feeling in use may be sticky.

<(B) Hydrophilic Thickener>

The (B) hydrophilic thickener in the oil-in-water emulsion composition of the present invention is not particularly limited as long as normally used in cosmetic products. Examples include natural or semi-synthetic water-soluble polymers, synthetic water-soluble polymers and inorganic water-soluble polymers.

As the natural or semi-synthetic water-soluble polymers, polysaccharides and derivatives thereof (including water-soluble alkyl-substituted polysaccharide derivatives) are preferably used. Specific examples include plant-based polymers such as gum arabic, tragacanth gum, galactan, guar gum, carob gum, karaya gum, carrageenan, pectin, agar, quince seed (marmelo), algecolloid (phaeophyceae extract), starch (rice, corn, potato, wheat) and glycyrrhizic acid; microbe-based polymers such as xanthan gum, dextran, succinoglycan and pullulan; starch-based polymers such as carboxymethyl starch and methylhydroxypropyl starch; cellulose-based polymers such as methyl cellulose, nitrocellulose, ethyl cellulose, methyl hydroxypropyl cellulose, hydroxyethyl cellulose, sodium cellulose sulfate, hydroxypropyl cellulose, sodium carboxymethyl cellulose (CMC), crystalline cellulose and cellulose powder; and alginic acid-based polymers such as sodium alginate and propylene glycol esters of alginic acid.

The synthetic water-soluble polymers include ionic or non-ionic water-soluble polymers, for example, vinyl-based polymers such as polyvinyl alcohol, polyvinyl methyl ether, polyvinyl pyrrolidone and carboxyvinyl polymers (carbomers); polyoxyethylene-based polymers such as polyethylene glycol (molecular weight 1500, 4000, 6000); copolymer-based polymers such as polyoxyethylene/polyoxypropylene copolymers; acryl-based polymers such as sodium polyacrylate, poly ethyl acrylate, polyacrylamide compounds and acrylic acid/alkyl methacrylate copolymers (product name "pemulen TR-1"); and polyethylene imine and cationic polymers.

The polyacrylamide compounds particularly include polyacrylamide compounds consisting of homopolymers, copolymers or crosspolymers containing one or more constituent units selected from the group consisting of 2-acrylamido-2-methylpropane sulfonic acid (hereinafter sometimes abbreviated to "AMPS"), acrylic acid and derivatives thereof.

Specific examples of such polyacrylamide compounds include vinylpyrrolidone/2-acrylamido-2-methylpropane sulfonic acid (salt) copolymers, dimethylacrylamide/2-acrylamido-2-methylpropane sulfonic acid (salt) copolymers, acrylamide/2-acrylamido-2-methylpropane sulfonic acid copolymers, dimethylacrylamide/2-acrylamido-2-methylpropane sulfonic acid crosspolymers crosslinked with methylenebisacrylamide, mixtures of polyacrylamide and sodium polyacrylate, sodium acrylate/2-acrylamido-2-methylpropane sulfonic acid copolymers, hydroxyethyl acrylate/2-acrylamido-2-methylpropane sulfonic acid (salt) copolymers, ammonium polyacrylate, polyacrylamide/ammonium acrylate copolymers, and acrylamide/sodium acrylate copolymers. However, the compounds are not limited to these examples.

Preferred examples of salts in the previous paragraph include alkali metal salts (such as calcium salts and magnesium salts), ammonium salts, organic amine salts (such as monoethanolamine salts, diethanolamine salts, triethanolamine salts and triethanolamine salts). One or more of these polyacrylamide compounds may be used.

These polyacrylamide compounds may be synthesized or obtained as commercial products. For example, the vinyl pyrrolidone/2-acrylamido-2-methylpropane sulfonic acid (salt) copolymer may be "Aristoflex AVC" (manufactured by Clariant), the sodium arylate/2-acrylamido-2-methylpropane sulfonic acid (salt) copolymer may be "Simulgel EG" (manufactured by Sepic) or "Simulgel EPG" (manufactured by Sepic), the acrylamide/2-acrylamido-2-methylpropane sulfonic acid sodium salt copolymer may be "Simulgel 600" (manufactured by Sepic), the acrylamide/2-acrylamido-2-methylpropane sulfonic acid (salt) may be "Sepigel 305" (manufactured by Sepic) or "Sepigel 501" (manufactured by Sepic), the homopolymer of a 2-acrylamido-2-methylpropane sulfonic acid sodium salt may be "Hostacerin AMPS" (manufactured by Clariant) or "Simulgel 800" (manufactured by Sepic), and the dimethylacrylamide/2-acrylamido-2-methylpropane sulfonic acid may be "SU-Polymer G-1" (manufactured by Toho Chemical Industry).

In the present invention, a crosspolymer of dimethylacrylamide and an acryloyl dimethyl taurine salt is particularly preferred, a specific example being a (dimethylacrylamide/sodium acryloyl dimethyl taurate) crosspolymer.

Examples of inorganic water-soluble polymers include bentonite, Al—Mg silicate (product name "Veegum"), laponite, hectorite and silicic anhydride.

The (B) hydrophilic thickener in the oil-in-water emulsion composition of the present invention may be a combination of one or more types. In particular, it is preferable to include at least one type selected from the group consisting of polysaccharides such as succinoglycan, xanthan gum and carboxymethylcellulose, derivatives thereof, and polyacrylamide compounds. When an ionic water-soluble polymer is added, rather than using it alone, the emulsion stability over time can be improved by blending it in combination with a polysaccharide or derivative thereof, or a polyacrylamide compound.

The blended amount of the (B) hydrophilic thickener in the oil-in-water emulsion composition of the present invention should preferably be at least 0.01% by mass, at least 0.03% by mass, at least 0.05% by mass, at least 0.08% by mass or at least 0.1% by mass, and at most 3% by mass, at most 4% by mass, at most 2% by mass or at most 1% by mass with respect to the total amount of the cosmetic. The specific range of the blended amount should be 0.01 to 3% by mass, preferably 0.05 to 3% by mass, and more preferably 0.1 to 1% by mass. If the blended amount is less than 0.01% by mass, there may be cases in which a stable oil-in-water emulsion composition cannot be obtained, and if more than 3% by mass is blended, there may be a heavy texture at the time of application.

<(C) Hydrophobically Treated Metal Oxide>

The (C) hydrophobically treated metal oxide in the oil-in-water emulsion composition of the present invention is a powder particle having a metal oxide powder particle as the base material, the surface of which is subjected to a hydrophobic treatment.

Examples of the base materials for the (C) hydrophobically treated metal oxide include titanium oxide, iron oxide, magnesium oxide, zinc oxide, calcium oxide and aluminum oxide. Additionally, a composite powder particle comprising a plurality of base materials may also be used.

The hydrophobic treatment to be performed on the base material powder particles may include various surface treatments that can be used as a surface treatment for powders blended into cosmetics and the like. For example, a fluorine compound treatment, a silicone treatment, a silane coupler treatment, a titanium coupler treatment, an oil treatment, an N-acylated lysine treatment, a polyacrylic acid treatment, an amino acid treatment, an inorganic compound treatment, a plasma treatment, a mechanochemical treatment, a silane compound or a silazane compound may be used. However, there may be cases in which the desired dispersibility is not obtained when the hydrophobic treatment is performed using a metal soap such as aluminum stearate. Therefore, the (C) hydrophobically treated metal oxide in the present invention refers to a "metal oxide hydrophobically treated without using a metal soap".

Particularly preferred as a hydrophobic treatment for a metal oxide powder in the present invention is a silicone treatment or a dextrin fatty acid treatment.

Examples of silicone treatments include treatments using silicone oils such as methylhydrogen polysiloxane, dimethylpolysiloxane (dimethicone) and methylphenylpolysiloxane; alkylsilanes such as methyltriethoxysilane, ethyltriethoxysilane, hexyltriethoxysilane and octyltriethoxysilane; and fluoroalkylsilanes such as trifluoromethylethyltrimethoxysilane and heptadecafluorodecyl trimethoxysilane.

An example of a dextrin fatty acid treatment is a treatment using dextrin palmitate or the like. Such hydrophobic treatments can be performed in accordance with conventional methods, and one or a combination of two or more hydrophobic treatment agents may be used.

The shape and size of the (C) hydrophobically treated metal oxide are not particularly limited, and for example, shapes such as spherical, plate-shaped, petal-shaped, flake-shape, rod-shaped, spindle-shaped, needle-shaped and irregularly shaped are possible. As the size of the (C) hydrophobically treated metal oxide, one having an average particle size of about 2 nm to 5 μm by spherical particle conversion is preferably used, and fine particle (average particle size=about 1 μm or less) titanium oxide or zinc oxide are preferred.

The (C) hydrophobically treated metal oxide used in the present invention may be one that is commercially available, examples of which include Finex-50W-LP2, STR-100C-LP (manufactured by Sakai Chemical Industry), MPY-1133M, MZX-3040TS and MTY-110M3S (manufactured by Tayca).

The blended amount of the (C) hydrophobically treated metal oxide in the oil-in-water emulsion composition of the present invention should preferably be at least 0.5% by mass, at least 1% by mass, at least 2% by mass, at least 3% by mass, at least 4% by mass or at least 5% by mass, and at most 35% by mass, at most 30% by mass, at most 25% by mass or at most 20% by mass with respect to the total amount of the oil-in-water emulsion composition of the present invention. The specific range of the blended amount should be 0.5 to 35% by mass, preferably 3 to 25% by mass, and more preferably 5 to 20% by mass. If the blended amount is less than 0.5% by mass, the effect of including the powder is not adequately achieved, and if the blended amount is more than 30% by mass, there is a tendency for problems in feeling in use to occur, such as squeakiness, unevenness and stickiness.

<(D) Non-Volatile Oil Other than Silicone Oil>

The non-volatile oil other than a silicone oil is an oil that is normally used in cosmetics or skin-care preparations for external use, selected from the group consisting of oils that are liquid, solid or semi-solid at ambient temperature and ambient pressure, and it can be a single type or a mixture of two or more types. The "non-volatile oil" in the present specification refers to an oil having a boiling point higher than about 250° C. Specifically, hydrocarbon oils, ester oils, vegetable oils, higher alcohols, higher fatty acids and oil-soluble UV-absorbing agents are included.

Examples of hydrocarbon oils include liquid paraffin, paraffin, squalane, squalene, pristane and vaseline.

Examples of ester oils include isopropyl myristate, cetyl octanoate, octyldodecyl myristate, isopropyl palmitate, butyl stearate, hexyl laurate, myristyl myristate, decyl oleate, hexyldecyl dimethyloctanoate, cetyl lactate, myristyl lactate, lanolin acetate, isocetyl stearate, isocetyl isostearate, cholesteryl 12-hydroxystearate, ethylene glycol di-2-ethylhexanoate, dipentaerythritol fatty acid ester, N-alkylglycol monoisotearate, neopentyl glycol dicaprate, diisostearyl malate, glycerin di-2-heptylundecanoate, trimethylolpropane tri-2-ethylhexanoate, trimethylelpropane triisostearate, glycerin trioctanoate, glycerin triisopalmitate, trimethylolpropane triisostearate, cetyl 2-ethylhexanoate, pentaerythritol tetra-2-ethylhexanoate, glycerin tri-2-ethylhexanoate, 2-ethylhexyl palmitate, glycerin trimyristate, tri-2-heptylundecanoic acid glycerides, castor oil fatty acid methyl esters, oleyl oleate, acetoglycerides, 2-heptylundecyl palmitate, diisobutyl adipate, N-lauroyl-L-glutamate-2-octyldodecyl ester, di-2-heptylyundecyl adipate, ethyl laurate, di-2-ethylhexyl sebacate, 2-hexyldecyl myristate, 2-hexyldecyl palmitate, di-2-hexyldecyl adipate, diisopropyl sebacate and triethyl citrate.

Examples of vegetable oils include avocado oil, camellia oil, macadamia nut oil, corn oil, olive oil, rapeseed oil, sesame oil, castor oil, peanut oil, almond oil, soybean oil, tea seed oil, jojoba oil and germ oil.

Examples of higher alcohols include oleyl alcohol, isostearyl alcohol, octyldodecanol, decyltetradecanol, jojoba alcohol, cetyl alcohol and myristyl alcohol, and examples of higher fatty acids include oleic acid, isostearic acid, linolic acid, linoleic acid, eicosapentaenoic acid, docosahexaenoic acid, palmitic acid and stearic acid.

Examples of oil-soluble UV-absorbing agents are not particularly limited as long as they are normally used in cosmetic products. For example, UV-absorbing agents selected from the group consisting of octocrylene, octyl-methoxycinnamate, 4-tert-butyl-4'-methoxydibenzoyl methane, methylene bis-benzotriazolyl tetramethylbutylphenol, bis-ethylhexyloxyphenol methoxyphenyl triazine, diethylamino hydroxybenzoyl hexyl benzoate, ethylhexyl triazone, diethylhexyl butamido triazone, 2-hydroxy-4-methoxybenzophenone, benzalmalonate and benzotriazole can be used in appropriate combinations.

The blended amount of the (D) non-volatile oil other than a silicone oil in the oil-in-water emulsion composition of the present invention should preferably be at least 1% by mass, at least 2% by mass, at least 3% by mass, at least 4% by mass or at least 5% by mass, and at most 50% by mass, at most 40% by mass, at most 30% by mass, at most 25% by mass or at most 20% by mass with respect to the total amount of the oil-in-water emulsion composition of the present invention. The specific range of the blended amount should be 1 to 50% by mass, preferably 3 to 25% by mass, and more preferably 5 to 20% by mass. If the blended amount is less than 1% by mass, the stability becomes poor, and if more than 50% by mass is added, problems in the feeling in use, such as stickiness, tend to occur.

Additionally, since the composition of the present invention contains a hydrophobically treated metal oxide (UV-scattering agent), a high UV protection capability can be obtained even without adding a UV-absorbing agent, so it is not always necessary to add an oil-soluble UV-absorbing agent, but such agent may be added as the (D) non-volatile oil other than a silicone oil. When blending an oil-soluble UV-absorbing agent, the amount should preferably be at least 5% by mass, at least 7% by mass, at least 8% by mass, at least 9% by mass or at least 10% by mass, and at most 30% by mass, at most 28% by mass, at most 25% by mass, at most 22% by mass or at most 20% by mass with respect to the total amount of the oil-in-water emulsion composition of the present invention. Specific ranges of the blended amounts may, for example, be 5 to 30% by mass, more preferably 10 to 25% by mass, and even more preferably 10 to 20% by mass. If the blended amount of the oil-soluble UV-absorbing agent is less than 5% by mass, it is difficult to achieve adequate improvement of the UV protection effect due to addition of the UV-absorbing agent, and if the amount exceeds 30% by mass, the skin may become irritated.

<(E) Silicone Oil and/or Volatile Hydrocarbon Oil>

The oil-in-water emulsion composition of the present invention may include (E) a silicone oil and/or a volatile hydrocarbon oil within a range not compromising the dispersibilty of the powder and the feeling in use.

The silicone oil is selected from the group consisting of volatile and non-volatile linear, branched or cyclic silicone oils. Examples include methylpolysiloxane, methylphenylpolysiloxane, methylpolycyclosiloxane, methyl hydrogen polysiloxane, dimethylsiloxane, dimethylsiloxane-methyl (POE)siloxane copolymer, highly polymerized methylpolysiloxane, dimethylsiloxane-methyl(POP)siloxane copolymer, tetradecamethyl hexasiloxane, octamethyl trisiloxane, dimethylsiloxane-methylcetyloxysiloxane copolymer, decamethyltetrasiloxane, cyclopentasiloxane, octamethylcyclotetrasiloxane, decamethyleyclopentasiloxane, dodecamethylcyclohexasiloxane and hexadecamethylcycloheptasiloxane.

As the volatile hydrocarbon oil, a relatively low-molecular-weight hydrocarbon oil (boiling point about 250° C. or less) may be used, and specifically, light liquid isoparaffin, isododecane or isohexadecane may be used.

When a (E) silicone oil and/or volatile hydrocarbon oil is blended into the oil-in-water emulsion composition of the present invention, the total blended amount is limited to 8% by mass or less, and may, for example, be at most 7% by mass, at most 6% by mass, at most 5% by mass, at most 4% by mass, at most 3% by mass, at most 2% by mass or at most 1% by mass. The oil-in-water emulsion composition of the present invention includes embodiments not containing (E) a silicone oil and/or a volatile hydrocarbon oil. If the total blended amount of the (E) silicone oil and/or volatile hydrocarbon oil exceeds 8% by mass, the fresh feeling in use that is inherent in oil-in-water emulsion compositions may be lost, and the dispersion effect of the (C) hydrophobically treated metal oxide due to the (A) polyether-modified silicone may be inhibited.

Therefore, when blending the (E) silicone oil and/or volatile hydrocarbon oil, the component (E) should preferably not be mixed in the oil phase in which the (C) hydrophobically treated metal oxide is present, in other words, the oil phase containing the (A) polyether-modified silicone, the (C) hydrophobically treated metal oxide and (D) the non-volatile oil other than a silicone oil, and should preferably be present as separate oil droplets. For this reason, aside from those that are included in order to dilute commercially available products such as (A) polyether-modified silicones, the (E) silicone oil and/or volatile hydrocarbon oil should be preferably prepared in a form that is substantially not contained in an oil phase in which the (C) hydrophobically treated metal oxide is present.

<(F) Non-Ionic Surfactant>

The oil-in-water emulsion composition of the present invention preferably further includes a surfactant, especially a non-ionic surfactant. By including a non-ionic surfactant, the emulsion stability of the composition is further improved.

As non-ionic surfactants that can be blended in the composition of the present invention, those that are lipophilic or hydrophilic may be selected as appropriate in accordance with the form of the composition or the like.

Examples of lipophilic non-ionic surfactants include sorbitan fatty acid esters such as sorbitan mono-oleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate and diglycerol sorbitan tetra-2-ethylhexylate; glycerin and polyglycerin fatty acids such as glycerin mono-cottonseed oil fatty acid, glycerin monoerucate, glycerin sesquioleate, glycerin monostearate, glycerin pyroglutamate α,α'-oleate and glycerin malate monostearate; and propylene glycol fatty acid esters such as propylene glycol monostearate; as well as hydrogenated castor oil derivatives, glycerin alkyl ethers, polyoxyethylene and methylpolysiloxane copolymers.

Examples of hydrophilic non-ionic surfactants include POE alkyl ether, POE alkylphenyl ether, POE-POP alkyl ether, POE fatty acid esters, POE sorbitan fatty acid esters, POE glycerin fatty acid esters, POE castor oil or hydrogenated castor oil derivatives, POE beeswax-lanolin derivatives, alkanolamides, POE propylene glycol fatty acid esters, POE alkyl amines, POE fatty acid amides, sucrose fatty acid esters and polyether-modified silicones. Note that "POE" refers to polyoxyethylene and "POP" refers to polyoxypropylene, and they may be referred to in this way below.

Among the above-mentioned hydrophilic non-ionic surfactants, ethylene oxide adduct-type non-ionic surfactants having an HLB of at least 8 are particularly preferred. Examples include POE (10 to 50 moles) phytosterol ether, POE (10 to 50 moles) dihydrocholesterol ether, POE (10 to 50 moles) 2-octyldodecyl ether, POE (10 to 50 moles) decyltetradecyl ether, POE (10 to 50 moles) oleyl ether, POE (10 to 50 moles) cetyl ether, POE (5 to 30 moles) POP (5 to 30 moles) 2-decyltetradecyl ether, POE (10 to 50 moles) POP (2 to 30 moles) cetyl ether, POE (20 to 60 moles) sorbitan mono-oleate, POE (10 to 60 moles) sorbitan monoisostearate, POE (10 to 80 moles) glyceryl monoisostearate, POE (10 to 30 moles) glyceryl monostearate and POE (20 to 100) hydrogenated castor oil derivatives.

The non-ionic surfactant may be blended as one type or a combination of two or more types. The surfactant content in the composition of the present invention is not particularly limited, but is normally 0.1-10% by mass, preferably 0.1-5% by mass, more preferably 0.5-3% by mass with respect to the total amount of the oil-in-water emulsion composition.

The oil-in-water emulsion composition of the present invention may contain, in addition to the aforementioned components, other optional components that can be blended into an oil-in-water emulsion composition, within a range not interfering with the effects of the present invention. Examples of other optional ingredients include, but are not limited to, lipophilic thickeners, humectants, pH adjusters, neutralizers, antioxidants, preservatives, chelating agents, emollients, vegetable extracts, fragrances, pigments and various medicinal agents. In particular, lower alcohols such as ethanol and/or polyols such as 1,3-butylene glycol, dipropylene glycol and glycerin are preferred in view of the stability of the system. The lower alcohol content is preferably 1 to 30% by mass and the polyol content is preferably 0.1 to 15% by mass.

The oil-in-water emulsion composition of the present invention is obtained by mixing the (A) polyether-modified silicone and the (D) non-volatile oil other than a silicone oil, adding a powder portion containing the (C) hydrophobically treated metal oxide to this mixture, and mixing/stirring using an HM mixer or the like. Meanwhile, the water phase components including the (B) hydrophilic thickener are mixed to obtain the water phase. Finally, by adding the oil phase to the water phase while stirring with a homomixer or the like, the oil-in-water emulsion composition of the present invention can be obtained. Additionally, when (E) a silicone oil and/or volatile hydrocarbon oil is to be blended, it is separately added to the oil-in-water emulsion composition prepared as mentioned above, which is stirred again so as to be present as separate oil droplets without being substantially included in the oil phase in which the (C) hydrophobically treated metal oxide is present.

The oil-in-water emulsion composition of the present invention allows the (C) hydrophobically treated metal oxide to be stably dispersed without blending a high amount of oils, thereby allowing the fresh sensation that is inherent in oil-in-water emulsion compositions to be maintained. For this reason, by using a powder having UV protection capability such as a hydrophobic fine-particle titanium oxide or a hydrophobic fine particle zinc oxide as the (C) hydrophobically treated metal oxide, a sunscreen cosmetic having an excellent feeling in use can be obtained.

By additionally including a UV-absorbing agent as the (D) non-volatile oil in the oil-in-water emulsion composition of the present invention, a high UV protection capability can be obtained by achieving a synergistic effect with the hydrophobically treated metal oxide. For this reason, according to the oil-in-water emulsion composition of the present invention, a sunscreen cosmetic that excels in both the feeling in use and the UV protection effect can be obtained.

EXAMPLES

Herebelow, the present invention will be explained in further detail by providing specific examples, but the present invention is not limited to the following examples. Additionally, the blended amounts in the following examples are indicated in % by mass where not especially mentioned to be otherwise.

Examples 1 to 4 and Comparative Examples 1 to 3

Oil-in-water emulsion compositions were prepared by separately mixing a water phase portion and an oil phase portion, having the compositions shown in Table 1 below, so as to be respectively homogeneous, dispersing a powder portion in the oil phase portion using a homomixer, and adding the result to the water phase portion and emulsifying with a homomixer. The resulting samples were observed by their external appearance and by using an optical microscope (400×), to evaluate the dispersibility of the powder according to the following criteria.

<Evaluation Criteria>

A: The hydrophobically treated powder was homogeneously dispersed in the oil.

B: The hydrophobically treated powder was homogeneously dispersed by external appearance, but slight aggregation was observed when studied under an optical microscope.

C: Some aggregation of the hydrophobically treated powder was observed by external appearance.

D: Most of the hydrophobically treated powder was aggregated.

TABLE 1

| | | Ex. 1 | Ex. 2 | Ex. 3 | Ex. 4 | Comp. Ex. 1 | Comp. Ex. 2 | Comp. Ex. 3 |
|---|---|---|---|---|---|---|---|---|
| Water Phase Portion | Ion-exchanged water | bal | bal | bal | bal | bal | bal | bal |
| | 1,3-butylene glycol | 3 | 3 | 3 | 3 | 3 | 3 | 3 |
| | Succinoglycan | 0.2 | 0.2 | 0.2 | 0.2 | 0.2 | 0.2 | 0.2 |
| | Polyoxyethylene-60 hydrogenated castor oil | 1.5 | 1.5 | 1.5 | 1.5 | 1.5 | 1.5 | 1.5 |
| | Chelating agent | s.a. | s.a. | s.a. | s.a. | s.a. | s.a. | s.a. |
| | Buffer | s.a. | s.a. | s.a. | s.a. | s.a. | s.a. | s.a. |
| | Phenoxyethanol | 0.5 | 0.5 | 0.5 | 0.5 | 0.5 | 0.5 | 0.5 |
| Oil Phase Portion | Ethyl alcohol | 4.5 | 4.5 | 4.5 | 4.5 | 4.5 | 4.5 | 4.5 |
| | PEG/PPG-19/19 dimethicone (HLB (Si) = 7.7)*1 | 0.8 | — | — | — | — | — | — |
| | Decamethyl pentasiloxane*1 | 0.8 | — | — | — | — | — | — |
| | PEG/PPG-30/10 dimethicone (HLB (Si) = 12.2)*2 | — | 0.8 | — | — | — | — | — |
| | Dipropylene glycol*2 | — | 0.8 | — | — | — | — | — |
| | PEG-12 dimethicone (HLB (Si) = 7.7)*3 | — | — | 0.8 | — | — | — | — |
| | PEG-11 methyl ether dimethicone (HLB (Si) = 12.7)*4 | — | — | — | 0.8 | — | — | — |
| | PEG-10 dimethicone | — | — | — | — | 0.8 | — | — |

TABLE 1-continued

|  |  | Ex. 1 | Ex. 2 | Ex. 3 | Ex. 4 | Comp. Ex. 1 | Comp. Ex. 2 | Comp. Ex. 3 |
|---|---|---|---|---|---|---|---|---|
|  | (HLB (Si) = 4.5)*[5] |  |  |  |  |  |  |  |
|  | Sorbitan sesqui-isostearate (HLB = 4.8) | — | — | — | — | — | 0.8 | — |
|  | Polyoxyethylene sorbitan monostearate (HLB = 14.9) | — | — | — | — | — | — | 0.8 |
|  | Octylmethoxycinnamate | 5 | 5 | 5 | 5 | 5 | 5 | 5 |
|  | Pentaerythrityl tetraethylhexanoate | 5 | 5 | 5 | 5 | 5 | 5 | 5 |
| Powder Portion | Dimethicone/hydrogen dimethicone-treated silica-coated fine particle zinc oxide | 5 | 5 | 5 | 5 | 5 | 5 | 5 |
|  | Total | 100 | 100 | 100 | 100 | 100 | 100 | 100 |
| Eval. | Dispersibility of hydrophobically treated powder | A | A | A | A | C | D | D |

*[1]Product name: BY11-030 (manufactured by Toray Dow Corning)
*[2]Product name: BY25-339 (manufactured by Toray Dow Corning)
*[3]Product name: SH3773M (manufactured by Toray Dow Corning)
*[4]Product name: KF6011 (manufactured by Shin-etsu Chemical)
*[5]Product name: KF6017 (manufactured by Shin-etsu Chemical)

As demonstrated in Examples 1 to 4, while the homogeneous dispersion of the powder into the internal phase was possible when using the polyether-modified silicones having an HLB (Si) in the range of 5 to 14, homogeneous dispersion was not possible when the HLB (Si) was less than 5 (Comparative Example 1). Additionally, when a common surfactant other than the polyether-modified silicone was used, homogeneous dispersion of the powder was not possible, whether in Comparative Example 2 having a low HLB or Comparative Example 3 having a high HLB.

Examples 5 to 11 and Comparative Examples 4-8

Oil-in-water emulsion compositions were prepared by mixing a water phase portion and oil phase portion A having the compositions shown in the below-indicated Table 2 and Table 3 so as to be respectively homogeneous, dispersing the powder portion in the oil phase portion A using a homomixer, adding the result to the water phase portion, emulsifying with a homomixer, and finally adding oil phase portion B and emulsifying again using a homomixer. The resulting samples were evaluated for the dispersibility of the compositions according to the aforementioned criteria. The results are shown together in Table 2 and Table 3.

TABLE 2

|  |  | Ex. 5 | Ex. 6 | Ex. 7 | Ex. 8 | Comp. Ex. 4 | Comp. Ex. 5 |
|---|---|---|---|---|---|---|---|
| Water Phase Portion | Ion-exchanged water | bal | bal | bal | bal | bal | bal |
|  | Dipropylene glycol | 3 | 3 | 3 | 3 | 3 | 3 |
|  | Xanthan gum | 0.1 | 0.1 | 0.1 | 0.1 | 0.1 | 0.1 |
|  | (Dimethylacrylamide/Na acryloyl dimethyl taurate) crosspolymer | 0.7 | 0.7 | 0.7 | 0.7 | 0.7 | 0.7 |
|  | Polyoxyethylene-40 hydrogenated castor oil | 0.5 | 0.5 | 0.5 | 0.5 | 0.5 | 0.5 |
|  | PEG-60 glyceryl isostearate | 0.2 | 0.2 | 0.2 | 0.2 | 0.2 | 0.2 |
|  | Chelating agent | s.a. | s.a. | s.a. | s.a. | s.a. | s.a. |
|  | Buffer | s.a. | s.a. | s.a. | s.a. | s.a. | s.a. |
|  | Phenoxyethanol | 0.5 | 0.5 | 0.5 | 0.5 | 0.5 | 0.5 |
| Oil Phase Portion A | Ethyl alcohol | 8 | 8 | 8 | 8 | 8 | 8 |
|  | PEG-12 dimethicone (HLB (Si) = 7.7)*[3] | 1.5 | 1.5 | 1.5 | 1.5 | 1.5 | 1.5 |

TABLE 2-continued

|  |  | Ex. 5 | Ex. 6 | Ex. 7 | Ex. 8 | Comp. Ex. 4 | Comp. Ex. 5 |
|---|---|---|---|---|---|---|---|
|  | Octylmethoxycinnamate | 15 | — | — | — | — | — |
|  | Liquid paraffin | — | 15 | — | — | — | — |
|  | Pentaerythrityl tetraethylhexanoate | — | — | 15 | — | — | — |
|  | Isopropyl myristate | — | — | — | 15 | — | — |
|  | Isododecane | — | — | — | — | 15 | — |
|  | Decamethyl cyclopentasiloxane | — | — | — | — | — | 15 |
|  | Volatile dimethicone*6 | — | — | — | — | — | — |
|  | Methylphenyl polysiloxane | — | — | — | — | — | — |
| Oil Phase Portion B | Non-volatile dimethicone*7 | — | — | — | — | — | — |
| Powder Portion | Dimethicone/hydrogen dimethicone-treated fine particle titanium oxide | 10 | 10 | 10 | 10 | 10 | 10 |
|  | Total | 100 | 100 | 100 | 100 | 100 | 100 |
| Eval. | Dispersibility of hydrophobically treated powder | A | A | A | A | D | D |

*3Product name: SH3773M (manufactured by Toray Dow Corning)
*6Product name: KF-96L-1.5cs (manufactured by Shin-etsu Chemical)
*7Product name: KF-96A-20cs (manufactured by Shin-etsu Chemical)

TABLE 3

|  |  | Comp. Ex. 6 | Comp. Ex. 7 | Ex. 9 | Ex. 10 | Ex. 11 | Comp. Ex. 8 |
|---|---|---|---|---|---|---|---|
| Water Phase Portion | Ion-exchanged water | bal | bal | bal | bal | bal | bal |
|  | Dipropylene glycol | 3 | 3 | 3 | 3 | 3 | 3 |
|  | Xanthan gum | 0.1 | 0.1 | 0.1 | 0.1 | 0.1 | 0.1 |
|  | (Dimethylacrylamide/ Na acryloyl dimethyl taurate) crosspolymer | 0.7 | 0.7 | 0.7 | 0.7 | 0.7 | 0.7 |
|  | Polyoxyethylene-40 hydrogenated castor oil | 0.5 | 0.5 | 0.5 | 0.5 | 0.5 | 0.5 |
|  | PEG-60 glyceryl isostearate | 0.2 | 0.2 | 0.2 | 0.2 | 0.2 | 0.2 |
|  | Chelating agent | s.a. | s.a. | s.a. | s.a. | s.a. | s.a. |
|  | Buffer | s.a. | s.a. | s.a. | s.a. | s.a. | s.a. |
|  | Phenoxyethanol | 0.5 | 0.5 | 0.5 | 0.5 | 0.5 | 0.5 |
| Oil Phase Portion A | Ethyl alcohol | 8 | 8 | 8 | 8 | 8 | 8 |
|  | PEG-12 dimethicone (HLB (Si) = 7.7)*3 | 1.5 | 1.5 | 1.5 | 1.5 | 1.5 | 1.5 |
|  | Octylmethoxycinnamate | — | — | 5 | 5 | 5 | 5 |
|  | Liquid paraffin | — | — | — | — | — | — |
|  | Pentaerythrityl tetraethylhexanoate | — | — | — | — | — | — |
|  | Isopropyl myristate | — | — | 5 | 5 | 5 | 5 |
|  | Isododecane | — | — | — | — | — | — |
|  | Decamethyl cyclopentasiloxane | — | — | — | — | — | — |
|  | Volatile dimethicone*6 | 15 | — | — | — | — | — |
|  | Methylphenyl polysiloxane | — | 15 | — | — | — | — |
| Oil Phase Portion B | Non-volatile dimethicone*7 | — | — | 2 | 5 | 8 | 10 |
| Powder Portion | Dimethicone/hydrogen dimethicone-treated fine particle titanium oxide | 10 | 10 | 10 | 10 | 10 | 10 |
|  | Total | 100 | 100 | 100 | 100 | 100 | 100 |
| Eval. | Dispersibility of hydrophobically treated powder | D | D | A | A | B | D |

*3Product name: SH3773M (manufactured by Toray Dow Corning)
*6Product name: KF-96L-1.5cs (manufactured by Shin-etsu Chemical)
*7Product name: KF-96A-20cs (manufactured by Shin-etsu Chemical)

As demonstrated in Examples 5 to 8, when a non-volatile oil other than silicone oil was added as the oil, homogeneous dispersion of the hydrophobically treated powder into the internal phase was possible, but homogeneous dispersion was not possible in Comparative Examples 4-7 using silicone oils or volatile hydrocarbon oils. On the other hand, when the silicone oil was added as separate oil droplets, as shown in Examples 9-11 and Comparative Example 8, homogeneous dispersion was possible when the volatile oil content was 8% by mass or less, but homogeneous dispersion was not possible when 8% by mass was exceeded.

Examples 12 to 14 and Comparative Examples 9 and 10

Oil-in-water emulsion compositions having the compositions shown in Table 4 below were prepared using methods similar to the above-described Example 1, and the dispersibility of each composition was evaluated in accordance with the aforementioned criteria. The results are shown together in Table 4.

As demonstrated by Examples 12 to 14, dispersion of the powder into the internal phase is good when the surface treating agent of the metal oxide is a silicone or dextrin palmitate, among which the silicone treatment exhibited extremely good dispersibility. On the other hand, homogeneous dispersion into the oil phase was not obtained when using an aluminum stearate-treated or untreated powder as demonstrated by Comparative Examples 9 and 10.

Examples 15-17

Oil-in-water emulsion compositions having the compositions shown in Table 5 below were prepared using the same methods as the above-described Example 1, and the dispersibility of each composition was evaluated in accordance with the aforementioned criteria. The results are shown together in Table 5.

TABLE 4

| | | Ex. 12 | Ex. 13 | Ex. 14 | Comp. Ex. 9 | Comp. Ex. 10 |
|---|---|---|---|---|---|---|
| Water Phase Portion | Ion-exchanged water | bal | bal | bal | bal | bal |
| | Glycerin | 2 | 2 | 2 | 2 | 2 |
| | Carboxymethylcellulose | 0.1 | 0.1 | 0.1 | 0.1 | 0.1 |
| | Succinoglycan | 0.1 | 0.1 | 0.1 | 0.1 | 0.1 |
| | (Dimethylacrylamide/Na acryloyl dimethyl taurate) crosspolymer | 0.2 | 0.2 | 0.2 | 0.2 | 0.2 |
| | Polyoxyethylene-60 hydrogenated castor oil | 2 | 2 | 2 | 2 | 2 |
| | Chelating agent | s.a. | s.a. | s.a. | s.a. | s.a. |
| | Buffer | s.a. | s.a. | s.a. | s.a. | s.a. |
| | Phenoxyethanol | 0.5 | 0.5 | 0.5 | 0.5 | 0.5 |
| Oil Phase Portion | 1,3-butylene glycol | 5 | 5 | 5 | 5 | 5 |
| | PEG-11 methyl ether dimethicone (HLB (Si) = 12.7)*4 | 3 | 3 | 3 | 3 | 3 |
| | Octylmethoxycinnamate | 5 | 5 | 5 | 5 | 5 |
| | Hydrogenated polydecene | 5 | 5 | 5 | 5 | 5 |
| Powder Portion | Dimethicone/hydrogen dimethicone-treated silicone-coated fine particle zinc oxide | 5 | — | — | — | — |
| | Tetrahydrotetramethyl cyclotetrasiloxane-treated iron oxide | 0.02 | — | — | — | — |
| | Octyltriethoxysilane-treated pigment-grade titanium oxide | — | 5 | — | — | — |
| | Dextrin palmitate-treated fine particle zinc oxide | — | — | 5 | — | — |
| | Stearic acid, aluminum hydroxide-treated fine particle titanium oxide | — | — | — | 5 | — |
| | Untreated fine particle zinc oxide | — | — | — | — | 5 |
| | Total | 100 | 100 | 100 | 100 | 100 |
| Eval. | Dispersibility of hydrophobically treated powder | A | A | B | D | D |

*4Product name: KF6011 (manufactured by Shin-etsu Chemical)

TABLE 5

|  |  | Ex. 15 | Ex. 16 | Ex. 17 |
|---|---|---|---|---|
| Water Phase Portion | Ion-exchanged water | bal | bal | bal |
|  | Succinoglycan | 0.2 | 0.2 | 0.2 |
|  | Polyoxyethylene-60 hydrogenated castor oil | 1.5 | 1.5 | 1.5 |
|  | Chelating agent | s.a. | s.a. | s.a. |
|  | Buffer | s.a. | s.a. | s.a. |
|  | Phenoxyethanol | 0.5 | 0.5 | 0.3 |
| Oil Phase Portion | Ethyl alcohol | 20 | 20 | 20 |
|  | PEG-12 dimethicone (HLB (Si) = 7.7) *3 | 3 | 3 | 3 |
|  | Octylmethoxycinnamate | 10 | 10 | 10 |
|  | Hydrogenated polydecene | 10 | 10 | 10 |
| Powder Portion | Dimethicone/hydrogen dimethicone-treated silica-coated zinc oxide | 5 | 20 | 30 |
|  | Total | 100 | 100 | 100 |

TABLE 5-continued

|  |  | Ex. 15 | Ex. 16 | Ex. 17 |
|---|---|---|---|---|
| Eval. | Dispersibility of hydrophobically treated powder | A | A | B |

*3 Product name: SH3773M (manufactured by Toray Dow Corning)

As demonstrated by Examples 15 to 17, homogeneous dispersion in the internal phase was possible even when the powder content was increased to 30%.

Examples 18 and 19 and Comparative Example 11

Oil-in-water emulsion compositions having the compositions shown in Table 6 below were prepared. However, Examples 18 and 19 were prepared using the same method as Example 1, while Comparative Example 11 was prepared using a homomixer in accordance with the method shown in Patent Document 1. The freshness of the resulting compositions was evaluated by 10 expert panelists according to the following criteria.

<Evaluation Criteria>

A: Evaluated as excellent by 8 to 10 panelists

B: Evaluated as excellent by 5 to 7 panelists

C: Evaluated as excellent by 4 or fewer panelists

Additionally, the change in appearance of the composition after 1 day of storage at 50° C. was evaluated by visual observation.

TABLE 6

|  | Ex. 18 | Comp. Ex. 11 | Ex. 19 |
|---|---|---|---|
| Ion-exchanged water | bal | bal | bal |
| Ethyl alcohol | 15 | 13 | 15 |
| Glycerin | 1 | 1 | 1 |
| 1,3-butylene glycol | 3 | 5 | 3 |
| Succinoglycan | 0.35 | 0.35 | — |
| Acrylic acid/alkyl methacrylate copolymer | — | — | 0.1 |
| (Dimethylacrylamide/Na acryloyl dimethyltaurate) crosspolymer | — | — | 0.5 |
| Polyoxyethylene-60 hydrogenated castor oil | 1.5 | 1.5 | 1.5 |
| Sorbitan sesquiisostearate | — | 0.5 | — |
| PEG/PPG-19/19 dimethicone (HLB (Si) = 7.7) *1 | 1 | — | 1 |
| Decamethylpentasiloxane *1 | 1 | — | 1 |
| Decamethylpentasiloxane | — | 12 | — |
| Isopropyl myristate | 3 | 3 | 3 |
| Isostearic acid | — | 0.5 | — |
| Triethoxycaprylylsilane-treated fine particle zinc oxide | 9 | 9 | 9 |
| Octylmethoxycinnamate | 8 | 8 | 8 |
| Bis-ethylhexyloxyphenol methoxyphenyl triazine | 1.5 | 1.5 | 1.5 |
| Diethylamino hydroxybenzoyl hexyl benzoate | 2 | 2 | 2 |
| Octocrylene | — | 3 | — |
| Phenoxyethanol | 0.5 | 0.5 | 0.5 |
| Neutralizing agent | — | s.a. | — |
| Chelating agent | s.a. | s.a. | s.a. |
| Buffer | s.a. | s.a. | s.a. |
| Fragrance | s.a. | s.a. | s.a. |
| Total | 100 | 100 | 100 |
| Freshness | A | C | A |
| Appearance change after 1 day at 50° C. | homogeneous | homogeneous | homogeneous |

*1 Product name: BY11-030 (manufactured by Toray Dow Corning)

From the above results, the oil-in-water emulsion compositions according to the present invention indicated in Examples 18 and 19 were able to achieve a much more fresh sensation in use than the conventional cosmetic using a volatile oil as shown in Comparative Example 11.

Furthermore, the UV shielding effects were compared for the compositions of Example 18 and Comparative Example 11. The comparative experiments of the UV shielding effect were performed by homogeneously applying 2 mg/cm$^2$ of the compositions onto a plate composed of PMMA, and the absorbance was measured with a spectrophotometer (Hitachi U-4100). Despite containing much less UV-protecting agent than Comparative Example 11, Example 18 exhibited a much higher UV protection effect as shown in FIG. 1.

Figure 2:
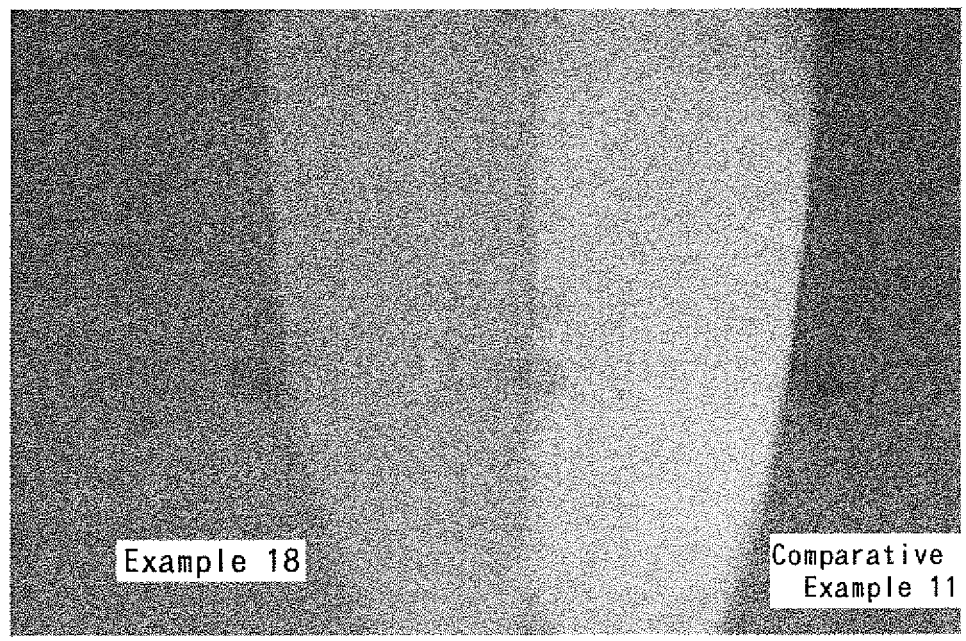
FIG. 2 A photograph comparing the transparency of formed films of Example 18 and Comparative Example 11.

Additionally, each composition was applied to an application thickness of 10 μm using a doctor blade. Photos of the applied film after drying for 15 minutes are shown in FIG. 2. Despite containing the same amount of powder, Example 18 was confirmed to have higher transparency than Comparative Example 11.

The above results show that, in the oil-in-water emulsion composition of the present invention, a sunscreen cosmetic having high UV protection effects and transparency of the applied film in addition to having a fresh feeling in use can be obtained by including an oil-soluble UV-absorbing agent.

Herebelow, formulation examples of the oil-in-water emulsion composition of the present invention are provided. Needless to say, the present invention is not in any way limited by these formulation examples, and is to be understood as being specified by the claims. The blended amounts are all indicated in % by mass with respect to the oil-in-water emulsion composition.

Formulation Example 1. Sunscreen Lotion

| (Component) | Blended amount (%) |
|---|---|
| Ion-exchanged water | bal |
| Glycerin | 5 |
| Dipropylene glycol | 3 |
| 1,3-butylene glycol | 3 |
| (PEG-240/decyltetradeceth-20/HDI) copolymer | 0.5 |
| Succinoglycan | 0.1 |
| Polyoxyethylene-100 hydrogenated castor oil | 2.5 |
| PEG-60 glyceryl isostearate | 0.5 |
| PEG-11 methyl ether dimethicone *6 | 2 |
| Pentaerythrityl tetraethylhexanoate | 5 |
| Mineral oil | 5 |
| Squalane | 10 |
| Dimethicone-treated silica-coated zinc oxide | 15 |
| Dimethicone/hydrogen dimethicone-treated titanium oxide | 5 |
| Tranexamic acid | 2 |
| Dipotassium glycyrrhizinate | 0.05 |
| Potassium 4-methoxysalicylate | 1 |
| Buffer | s.a. |
| Preservative | s.a. |

Formulation Example 2. Sunscreen Base

| (Component) | Blended amount (%) |
|---|---|
| Ion-exchanged water | bal |
| Ethyl alcohol | 5 |
| 1,3-butylene glycol | 3 |
| Succinoglycan | 0.1 |
| (Dimethylacrylamide/Na acryloyl dimethyltaurate) crosspolymer | 0.7 |
| PEG-12 dimethicone *5 | 1 |
| Octylmethoxycinnamate | 3 |
| Octocrylene | 2 |
| Ethylhexyl triazone | 0.5 |
| Oxybenzone-3 | 0.5 |
| t-Butyl methoxydibenzoylmethane | 0.5 |

-continued

| (Component) | Blended amount (%) |
|---|---|
| Phenylbenzimidazole sulfonic acid | 0.5 |
| Octyltriethoxysilane-treated titanium oxide | 4 |
| Octyltriethoxysilane-treated iron oxide | 2 |
| Dimethicone | 3 |
| Spherical silica | 2 |
| Chelating agent | s.a. |
| Buffer | s.a. |
| Preservative | s.a. |
| Antioxidant | s.a. |
| Fragrance | s.a. |

The invention claimed is:

1. An oil-in-water emulsified sunscreen cosmetic comprising:
    (A) 0.1 to 5% by mass of a polyether-modified silicone having an HLB (Si) of 5 to 14;
    (B) 0.1 to 2% by mass of one or more hydrophilic thickeners;
    (C) 1 to 30% by mass of a metal oxide hydrophobically treated with any one selected from the group consisting of methylhydrogen polysiloxane, dimethylpolysiloxane, methylphenylpolysiloxane, methyltriethoxysilane, ethyltriethoxysilane, hexyltriethoxysilane, octyltriethoxysilane, trifluoromethylethyl trimethoxysilane, heptadecafluorodecyl trimethoxysilane, a mixture of dimethylpolysiloxane and methylhydrogen polysiloxane, and dextrin palmitate; and
    (D) 5 to 40% by mass of a non-volatile oil other than a silicone oil;
wherein the (C) hydrophobically treated metal oxide is present in the internal phase, and the (D) non-volatile oil other than a silicone oil comprises an oil-soluble UV-absorbing agent.

2. The sunscreen cosmetic according to claim 1, wherein: the (B) hydrophilic thickener comprises at least one thickener selected from the group consisting of polysaccharides and derivatives thereof, and polyacrylamide compounds.

3. The sunscreen cosmetic according to claim 1, wherein: the (B) hydrophilic thickener comprises an ionic water-soluble polymer, and further comprises a polysaccharide or derivative thereof, or a polyacrylamide compound.

4. The sunscreen cosmetic according to claim 1, wherein: the (B) hydrophilic thickener comprises a polyacrylamide compound, and further comprises a polysaccharide or derivative thereof.

5. The sunscreen cosmetic according to claim 1, further comprising:
    (E) at least one of a silicone oil and a volatile hydrocarbon oil, in an amount of at most 8% by mass.

6. The sunscreen cosmetic according to claim 1, further comprising:
    (F) a non-ionic surfactant.

7. The composition according to claim 1, wherein the (C) hydrophobically treated metal oxide is hydrophobically treated with:
    (a) a mixture of dimethylpolysiloxane and methylhydrogen polysiloxane,
    (b) tetrahydrotetramethyl cyclotetrasiloxane,
    (c) octyltriethoxysilane, or
    (d) dextrin palmitate.

* * * * *